(12) United States Patent
Caizza

(10) Patent No.: US 7,115,114 B2
(45) Date of Patent: Oct. 3, 2006

(54) MEDICAL DEVICE HAVING RELEASABLE RETAINER

(75) Inventor: Richard J. Caizza, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 59 days.

(21) Appl. No.: 10/428,648

(22) Filed: May 2, 2003

(65) Prior Publication Data

US 2004/0220532 A1    Nov. 4, 2004

(51) Int. Cl.
 *A61M 5/00*    (2006.01)
(52) U.S. Cl. ............. 604/240; 604/243; 604/187; 604/181; 604/164.04; 604/164.07; 604/905; 604/264
(58) Field of Classification Search ............ 604/188, 604/263, 110, 164.04, 164.07, 181, 187, 192, 604/264, 533, 535, 240–243, 231, 905
See application file for complete search history.

(56) References Cited

U.S. PATENT DOCUMENTS

| | | | |
|---|---|---|---|
| 791,802 A | 6/1905 | De Lisle | |
| 1,591,762 A | 7/1926 | Haines | |
| 1,683,349 A * | 9/1928 | Hein | 604/241 |
| 1,683,350 A | 9/1928 | Hein | |
| 2,020,111 A | 11/1935 | Eisele | 128/221 |
| 2,034,294 A | 3/1936 | Hein | 128/215 |
| 2,088,338 A | 7/1937 | Popper et al. | 128/221 |
| 2,764,978 A | 10/1956 | Everett | 128/215 |
| 2,828,743 A | 4/1958 | Ashkenaz et al. | 128/218 |
| 2,834,346 A | 5/1958 | Adams | 128/218 |
| 2,902,995 A | 9/1959 | Loper | 128/215 |
| 3,043,304 A | 7/1962 | Higgins | 128/218 |
| 3,469,581 A | 9/1969 | Burke | 128/221 |
| 3,472,227 A | 10/1969 | Burke | 128/221 |
| 3,527,217 A | 9/1970 | Gettig | 128/221 |
| 4,040,421 A | 8/1977 | Young | 128/218 N |
| 4,281,653 A | 8/1981 | Barta et al. | 128/218 D |
| 4,430,080 A | 2/1984 | Pasquini et al. | 604/240 |
| 4,490,142 A | 12/1984 | Silvern | 604/241 |
| 4,589,871 A | 5/1986 | Imbert | 604/240 |
| 4,675,020 A | 6/1987 | McPhee | 604/411 |
| 4,747,839 A | 5/1988 | Tarello et al. | 604/240 |
| 4,822,343 A | 4/1989 | Beiser | 604/187 |
| 5,047,021 A | 9/1991 | Utterberg | 604/283 |
| 5,053,015 A | 10/1991 | Gross | 604/167 |
| 5,066,287 A | 11/1991 | Ryan | 604/240 |
| 5,312,377 A | 5/1994 | Dalton | 604/283 |

(Continued)

*Primary Examiner*—Kevin C. Sirmons
*Assistant Examiner*—Catherine N. Witczak
(74) *Attorney, Agent, or Firm*—Jeanne P. Lukasavage

(57) ABSTRACT

A medical device having a releasable retaining includes needle cannula connected to a hub having an open proximal end with a frusto-conically shaped cavity therein. The cavity is part of a passageway through the hub which is in fluid communication with the lumen of the needle cannula. A retaining element is releasably connected to the hub. The hub includes an aperture and at least one protuberance projecting into the aperture for engaging the frusto-conically shaped tip of a fluid delivery device. The protuberance is shaped to offer less resistance to hub movement in a direction of engagement than in a direction of disengagement with the tip. The retaining element is connected to the hub so that when the hub is engaged to the tip, the force required to disengage the retaining element from the tip is greater than the force required to disengage the retaining element from the hub.

15 Claims, 16 Drawing Sheets

U.S. PATENT DOCUMENTS

| | | | |
|---|---|---|---|
| 5,348,544 A | 9/1994 | Sweeney et al. | 604/192 |
| 5,405,340 A | 4/1995 | Fageol et al. | 604/283 |
| 5,458,580 A | 10/1995 | Hajishoreh | 604/240 |
| 5,466,223 A | 11/1995 | Bressler et al. | 604/110 |
| 5,637,101 A | 6/1997 | Shillington | 604/242 |
| 5,681,295 A | 10/1997 | Gyure et al. | 604/263 |
| 5,713,876 A | 2/1998 | Bogert et al. | 604/243 |
| 5,722,643 A | 3/1998 | Chamberlin et al. | 604/283 |
| 5,741,084 A * | 4/1998 | Del Rio et al. | 403/349 |
| 5,836,919 A | 11/1998 | Skurka et al. | 604/187 |
| 5,851,201 A | 12/1998 | Ritger et al. | 604/240 |
| 6,132,402 A | 10/2000 | Tessmann et al. | 604/240 |
| 6,217,560 B1 | 4/2001 | Ritger et al. | 604/243 |
| 6,436,076 B1 * | 8/2002 | Hsu | 604/240 |
| 6,629,774 B1 * | 10/2003 | Gruendeman | 366/336 |
| 2002/0138045 A1 | 9/2002 | Moen | 604/240 |

* cited by examiner

MEDICAL DEVICE HAVING RELEASABLE RETAINER

FIELD OF THE INVENTION

The present invention relates to a medical device such as a hypodermic needle assembly which is adapted to releasably engage a fluid transfer device such as a syringe. In particular, the present invention relates to a medical device such as a hypodermic needle assembly having a releasable retaining element for improving the connection between a needle assembly and a syringe.

BACKGROUND

A hypodermic syringe consists of a cylindrical barrel, most commonly made of thermoplastic material or glass, with a distal end adapted to be connected to a hypodermic needle and a proximal end adapted to receive a stopper and plunger rod assembly. The stopper provides a relatively air-tight seal between itself and the syringe barrel so that movement of the stopper up and down the barrel will cause liquid, blood or other fluids to be drawn into or forced out of the syringe through the distal end. The stopper is moved along the syringe barrel by applying axial force on a rigid plunger rod which is connected to the stopper and is sufficiently long to be accessible outside of the barrel.

Hypodermic needle assemblies, typically including a cannula and a hub, are often removably attached to syringes for performing a variety of tasks such as the delivery of medication into patients and into devices, and for withdrawing fluid samples from patients and from fluid sources. Usually, the hub of the hypodermic needle assembly has tapered interior surface adapted to engage the tapered tip of the syringe barrel so that the two components are joined in a frictional interference fit. The tapered syringe tip and the complementarily tapered receptacle in the hub are referred to as standard luer fittings. A wide variety of other medical devices such as stopcocks and tubing sets have standard luer fittings which allow them to be engaged to a syringe tip.

It is important that the frictional fit between the syringe tip and the needle hub or other medical device is strong enough to prevent accidental disengagement caused by the fluid pressures within the syringe and/or other factors such as forces applied to the needle hub when actuating safety needle shields connected to the hub. If the syringe tip becomes disengaged from the needle assembly, medication, blood or other fluids will be lost, and there is also potential for contamination.

The prior art teaches many structures for improving the connection between medical devices having tapered luer fittings such as needle assemblies and syringes. These structures include complementary engaging structure on both the needle hub and syringe barrel tip such as projections and recess providing for a snap-fit arrangement. Manually releasable locking structures are provided to increase the connection between the needle hub and barrel tip while allowing reasonable forces for disconnections of these components. Also, enhancements to the luer tip of the syringe barrel such as coatings, sandblasting and mechanical collars have provided for improved connection between a needle hub and a syringe barrel tip. Many of the structures taught by the prior art do not contemplate the subsequent removal of the needle assembly from the syringe barrel. Others require extensively modified needle hubs and barrel tips. Structures having a tapered luer fitting such as a needle assembly and syringe barrel are adequate for normal use when the needle assembly is properly installed on the syringe tip. Difficulties can arise if the user does not use enough force to frictionally engage the luer tapered surfaces which can result in inadvertent disconnection of the needle assembly.

Although the prior art teaches various devices and structures for improving the strength of the connection between a syringe barrel and the hub of a needle assembly or other fluid handling device, there is still a need for a simple, straight-forward, reliable needle hub or other fluid-handling device having structure which improves the strength of the connection with the syringe tip or other device having a standard tapered luer tip. There is also a need for a needle hub requiring consistent forces for disengagement even when less than the desired force is used for engagement.

SUMMARY OF THE INVENTION

The medical device having a releasable retainer of the present invention for use with a fluid transfer device having a frusto-conically shaped tip includes a hub having an open proximal end with a frusto-conically shaped cavity therein, a distal end and a passageway therethrough. The cavity is part of the passageway. A retaining element is releasably connected to the hub. The retaining element includes an aperture therein and at least one protuberance projecting into the aperture for engaging the frusto-conically shaped tip of the fluid transfer device. The protuberance is shaped to offer less resistance to hub movement in a direction of engagement than in a direction of disengagement with the tip. Structure for connecting the retaining element to the hub is also provided so that when the hub is in fluid-tight engagement with the tip, the force required to disengage the retaining element from the tip can be greater than the force required to engage the retaining element from the hub. The hub may also include a needle cannula having a proximal end, a sharp distal end and a lumen therethrough. The needle cannula is joined to the distal end of the hub so that the lumen in the cannula is in fluid communication with the passageway in the hub.

The retaining element may include a plurality of protuberances on the retaining elements. The structure for connecting the retaining element to the hub may include a wide variety of interference fits or structures or additional elements including, but not limited to, frangible links and adhesive. The protuberance can extend for 360° around the retaining element. The retaining element need not extend completely around the passageway of the hub. The needle assembly may include a pivotable needle shield having a cavity therein hingedly connected to the hub and capable of pivoting from a needle exposing position which allows access to the distal end of the needle cannula and a needle protecting position wherein the distal end of the needle cannula is within the cavity of the needle shield.

The medical device may be connected to a syringe barrel having an inside surface defining a chamber, an open proximal end and a distal end including an elongate frusto-conically shaped tip having a conduit therethrough. The needle assembly is connected to the syringe barrel so that the frusto-conically shaped tip is in fluid-tight engagement with the frusto-conically shaped cavity of the hub and the lumen is in fluid communication with the cavity.

Another alternative embodiment of the needle assembly of the present invention further includes a guide element on the hub having an aperture therethrough. An elongate barrier arm having a proximal end and a distal end is positioned in the aperture for sliding axial movement therein. The distal end of the barrier arm includes a barrier element having a distal end, a proximal end and a needle passageway therethrough. The needle cannula is positioned at least partially within the needle passageway of the barrier element. The barrier arm is movable from at least a first retracted position wherein the distal end of the needle cannula passes completely through the barrier element so that the distal end of the needle cannula is exposed, to a second extended position wherein the barrier element surrounds the distal end of the needle cannula to prevent incidental contact with the distal end of the needle cannula. A finger contact surface on the barrier arm is provided to accept digital force to the barrier arm to move the barrier arm into the second extended position.

Still another alternative embodiment of the needle assembly of the present invention further includes a needle guard having a proximal end, a distal end and a needle passageway therethrough. The needle guard is movable along the needle cannula from a first position substantially adjacent the proximal end of the needle cannula to a second position where a distal tip of the needle cannula is intermediate the opposed proximal and distal ends of the needle guard. A hinged arm having proximal and distal segments articulated to one another for movement between a first position wherein the segments are substantially collapsed onto one another and a second position where the segments are extended from one another is provided. The proximal segment of the hinged arm is articulated to a portion of the hub. The distal segment of the hinged arm is articulated to the needle guard. The proximal and distal segments of the hinged arm have respective lengths for permitting the guard to move from the first position to the second position on the needle cannula and for preventing the guard from moving distally beyond the second position. The components of the hinged arm may be integrally molded of thermoplastic material.

DETAILED DESCRIPTION

Figure 1:
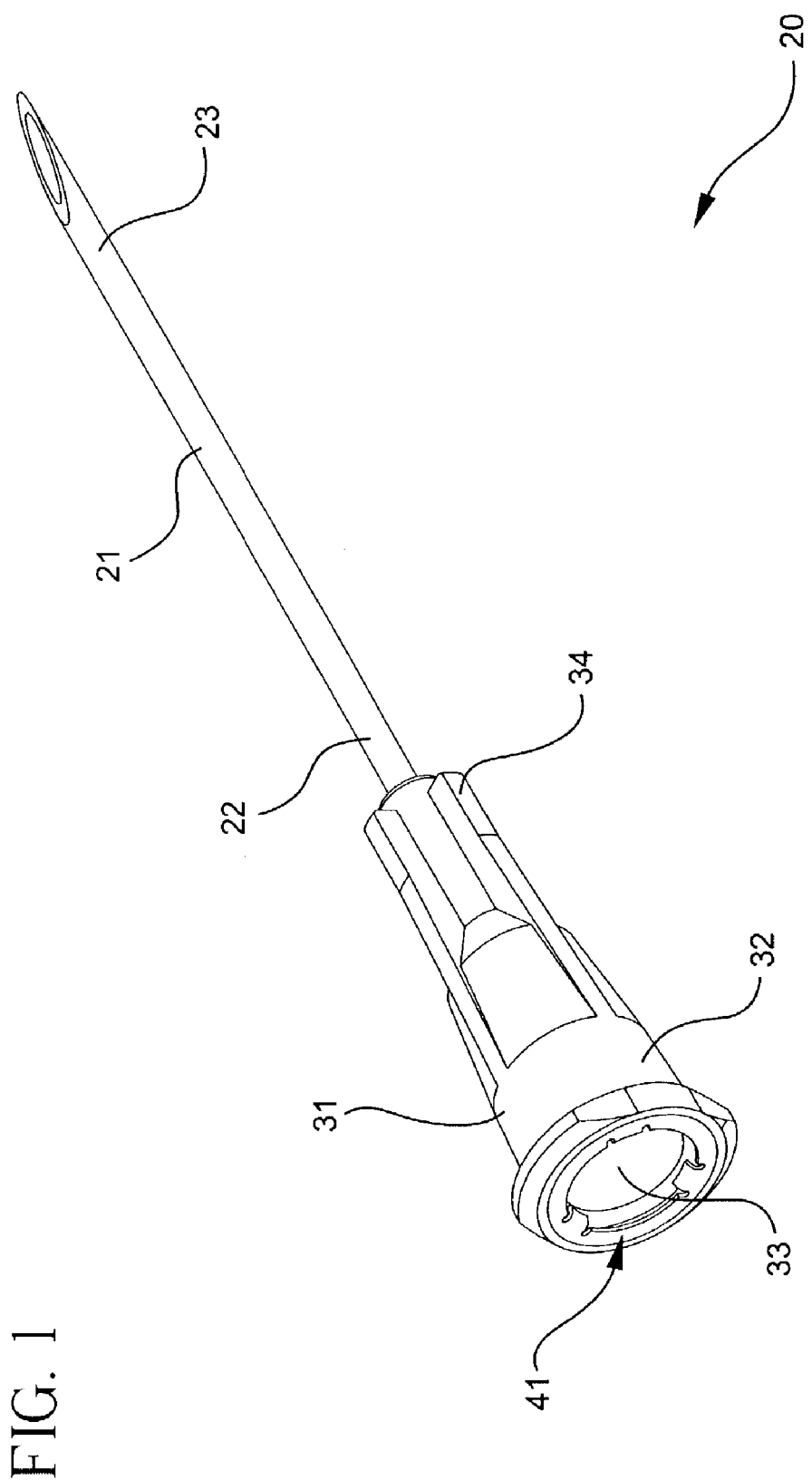
FIG. 1 is a perspective view of a needle assembly of the present invention.
Figure 2:
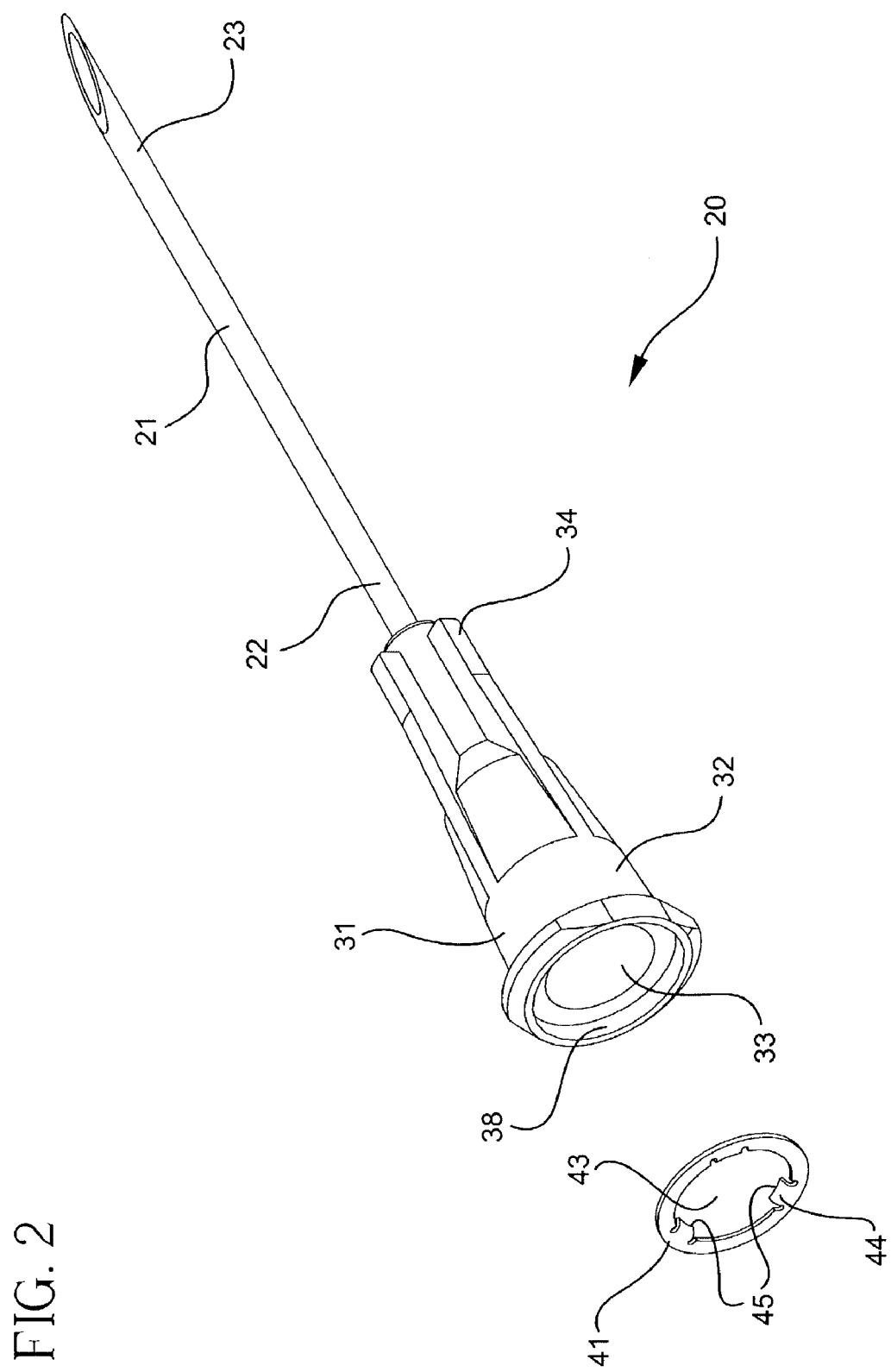
FIG. 2 is an exploded perspective view of the needle assembly of FIG. 1.
Figure 3:
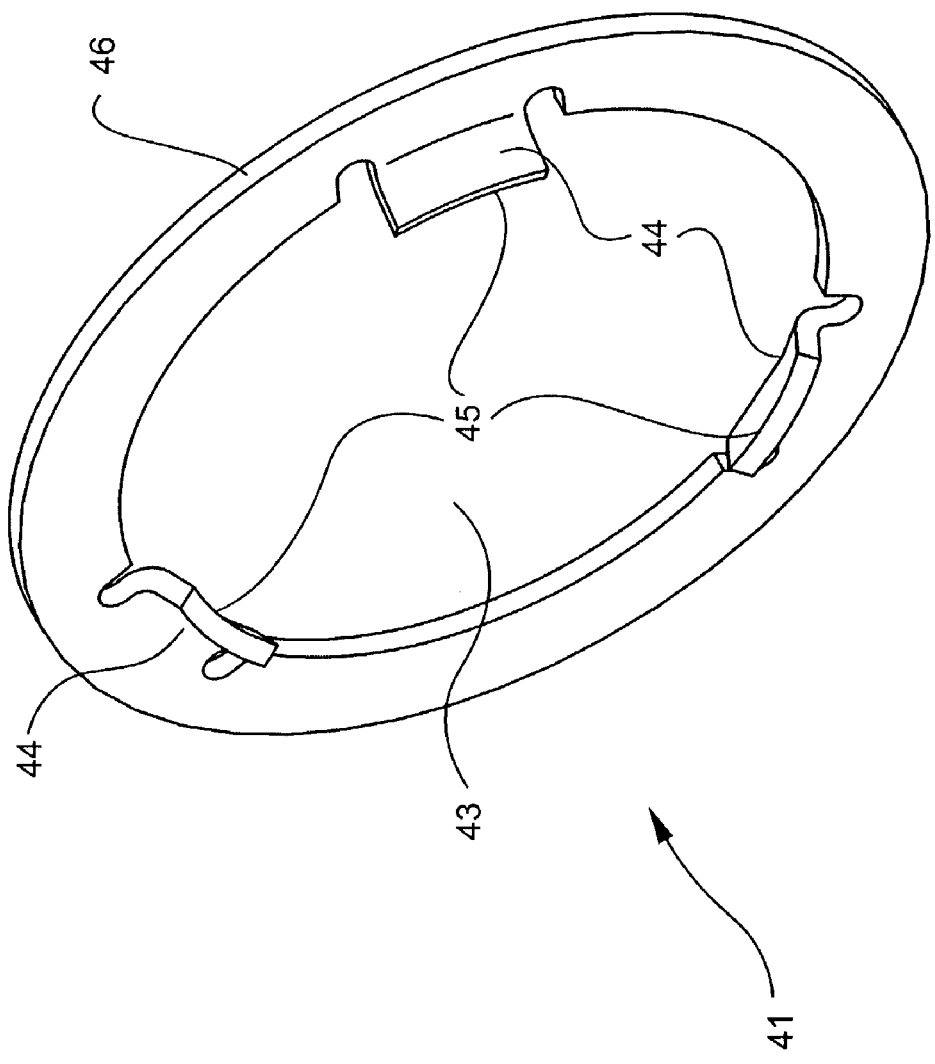
FIG. 3 is a perspective view of the retaining element of the needle assembly.
Figure 4:
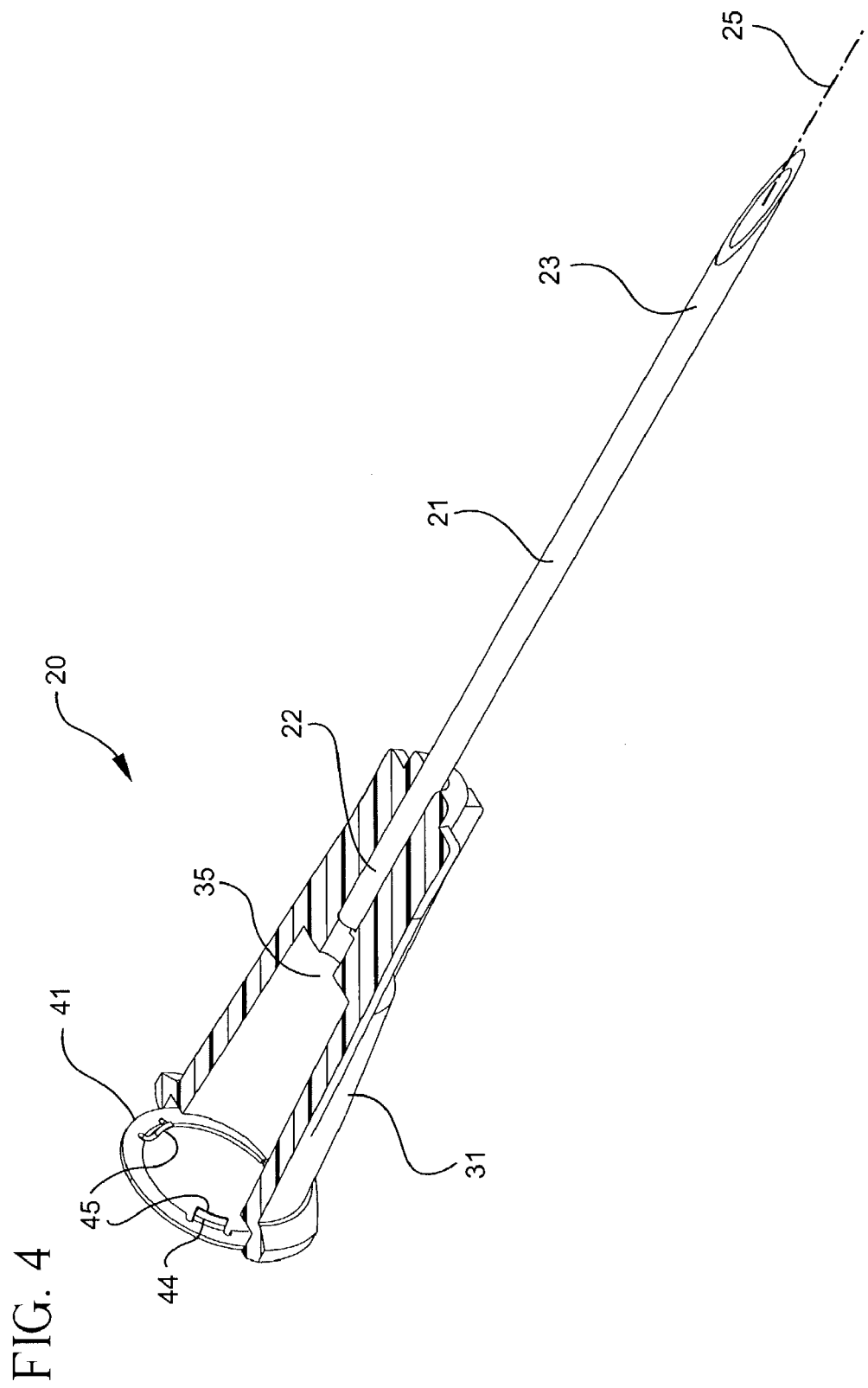
FIG. 4 is a partial cross-sectional perspective view of the needle assembly.
Figure 5:
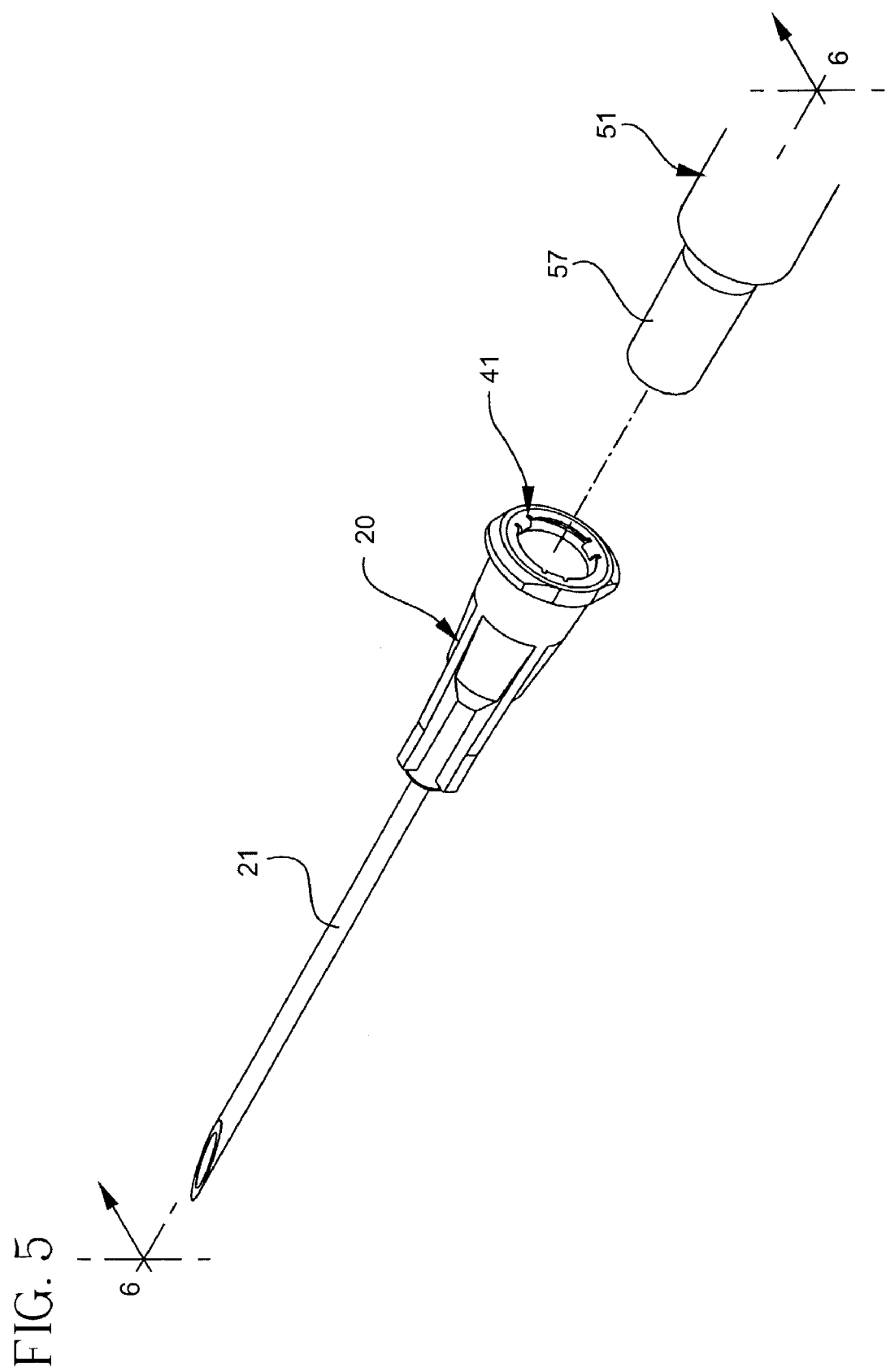
FIG. 5 is an exploded perspective view illustrating the needle assembly and a syringe barrel having a frusto-conically shaped tip.
Figure 6:
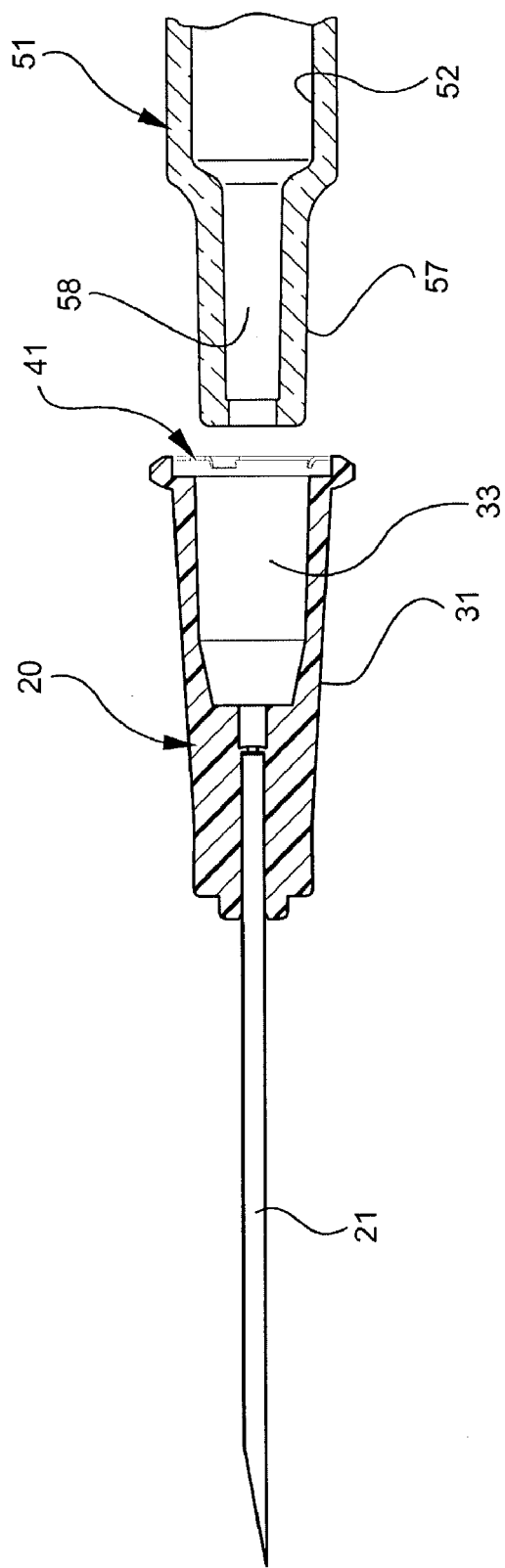
FIG. 6 is a partial cross-sectional view of the needle assembly and syringe barrel of FIG. 5 taken along line 6—6.

While this invention is satisfied by embodiments in many different forms, there are shown in the drawings and will herein be described in detail, preferred embodiments of the invention with the understanding that the present disclosure is to be considered exemplary of the principles of the invention and not intended to limit the invention to the embodiments illustrated. The scope of the invention will be measured by the appended claims and their equivalents.

Referring to FIGS. 1–8, a medical device such as needle assembly 20 includes a needle cannula 21 having a proximal end 22, a distal end 23 and a lumen 24 therethrough defining a longitudinal axis 25. A hub 31 includes an open proximal end 32 with a cavity 33 therein, a distal end 34 and a passageway 35 therethrough. The cavity is part of the passageway. The proximal end of the needle cannula is joined to the distal end of the hub so that the lumen of the needle cannula is in fluid communication with the passageway of the hub. Although not necessary, hub 31 may include radial projections 37 for engaging the locking-type collar of a syringe barrel or other fluid-delivery device.

Needle cannula 21 is preferably made of metal such as stainless steel and can be held to the hub using various manufacturing methods with adhesives such as epoxy being preferred. The hub is preferably made of injection moldable plastic such as polypropylene, polyethylene, polycarbonate and combinations thereof. The needle cannula and hub may be integrally formed of thermoplastic material. The needle assembly can be used with a variety of fluid transfer devices having a frusto-conically shaped luer tip such as a hypodermic syringe.

A syringe includes syringe barrel 51 having an inside surface 52 defining a chamber 53, an open proximal end 55 and a distal end 56 including an elongate frusto-conically shaped tip 57 having a conduit 58 therethrough. The needle assembly is connected to the syringe barrel so that the frusto-conically shaped tip is in fluid-tight engagement with the frusto-conically shaped cavity in the hub and the lumen is in fluid communication with the cavity. A concern with prior art needle assemblies and syringe barrels having complementary luer fittings is that the needle assembly may become loosened or disengaged from the syringe tip during use. This may happen because the user does not apply enough axial force to properly engage the needle hub to the barrel tip, and the hydraulic pressure of the injection process and/or forces induced during normal use dislodge the needle assembly from the barrel. Sometimes more than one needle is used with a syringe such as when a first needle is used to fill the syringe and the second is used for injection. With this use, any liquid medication inadvertently deposited on the barrel tip can change the frictional properties of the tip and increase the potential for unintended disengagement of the needle assembly.

The present invention provides a medical device having a fluid transfer fitting, such as a needle hub, which can be used with any standard luer slip fitting to provide improved retention of the needle assembly to the luer slip fitting and to allow for more uniform removal force as will be explained in detail hereinafter. This improvement is accomplished through the use of retaining element 41 which is releasably connected to hub 31. Retaining element 41 includes aperture 43 therein and at least one protuberance 44 projecting into the aperture for engaging the frusto-conically shaped tip of a syringe barrel for up to 360° of the aperture. The retaining element need not extend entirely around the cavity and it can be a discrete single element. Accordingly, the term "aperture" as used herein can include an opening or cut-out. In this preferred embodiment, there are three protuberances equally spaced around the aperture. The protuberance is shaped to offer less resistance to hub movement in a direction of engagement than in a direction of disengagement from a luer slip fitting such as a barrel tip. In this embodiment the directional bias is accomplished by distally and inwardly facing end 45 of protuberance 44. The distally-facing end portions of the protuberance will allow the needle assembly to be connected to the barrel tip with application of forces which are comparable to those using a hub without a retaining element. However, the end of the protuberance, which deflects slightly upon installation of the needle assembly, tends to engage the needle hub to prevent unintended disengagement of the needle assembly during use. Various materials and protuberance shapes can be used to form a retaining element so long as the force of engagement of the retaining element to the barrel tip is less than the force required to remove the retaining element from the barrel tip. An important feature of the present invention lies in the fact that there can be a substantial difference between the engagement force of the retaining element and the force required to dislodge the retaining element since the force required to remove the needle assembly from the barrel tip is controlled by means for connecting the retaining element to the hub.

In this embodiment, the force required to disconnect the retaining element from the hub is controlled by an interference fit between outside diameter 46 of the retaining element and inside diameter 38 of recess 39 in the hub. By carefully controlling the inside diameter of the hub recess and the outside diameter of the retaining element, the disengagement connection force can be controlled to be enough to retain the needle assembly during normal use while allowing easy removal of the needle assembly from the barrel tip. In this preferred embodiment, the retaining element is desirably made of metal which is preferably stainless steel. In this embodiment, the retaining element is formed from stainless steel sheet metal. It can be seen that the outside diameter of the retaining element could be formed in a fully or partial cylindrical shape to provide increased surface contact between the retaining element and the hub. The term "interference" or "interference fit" used to describe the connection between the retaining element and the hub is intended to include any manner of press-fit, snap-fit and variations thereof where the retaining element must overcome a physical engagement with the hub to release therefrom. Means for connecting as used herein is intended to include interferences and other means such as adhesives or frangible connections between the retaining element and hub which break upon application of the desired force. Means for connecting may also include a retaining element which is configured to engage an outside surface of the hub so that the interference is between the element and the outside of the hub. It may also include an additional element between the retaining element and the hub. All of these variations fall within the purview of the present invention and the interference fit of the metal retaining element to the hub is merely representative of these many possibilities.

Figure 7:
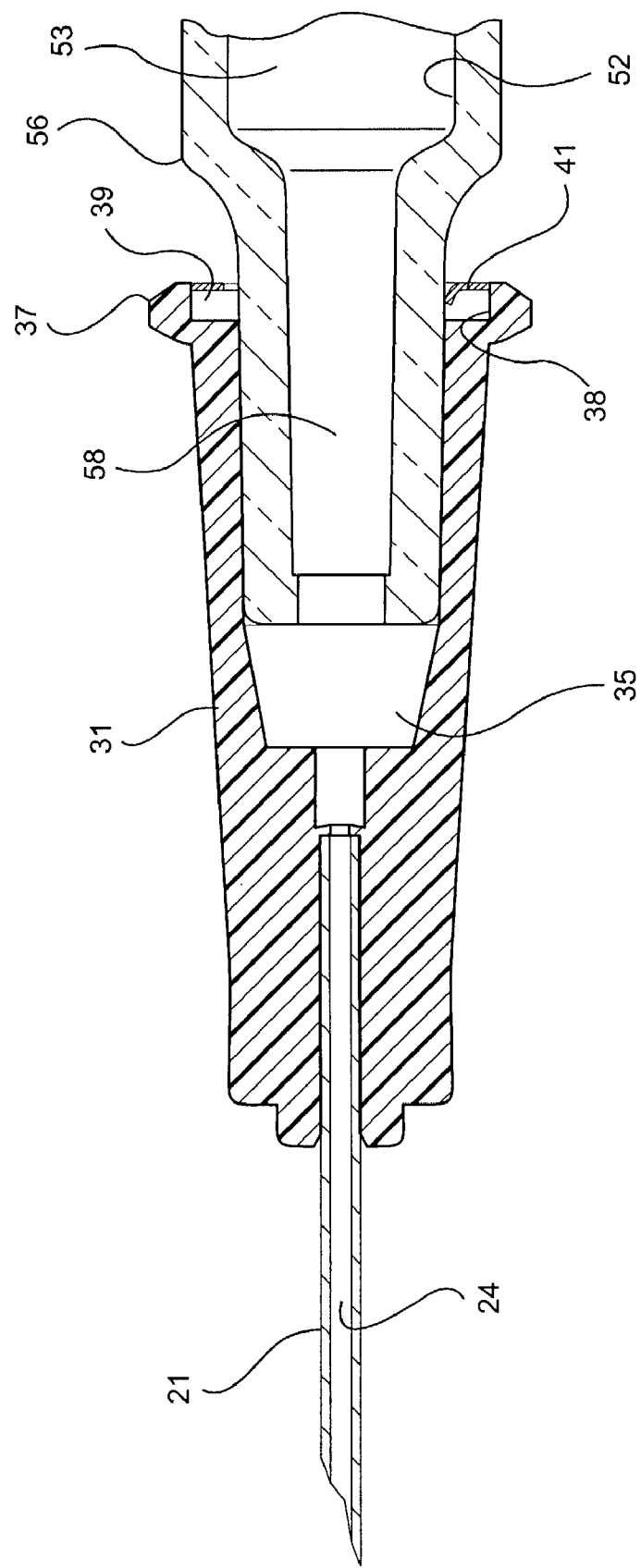
FIG. 7 illustrates the needle assembly and syringe barrel of FIG. 6 connected so that the lumen of the needle is in fluid communication with the chamber of the barrel.
Figure 8:
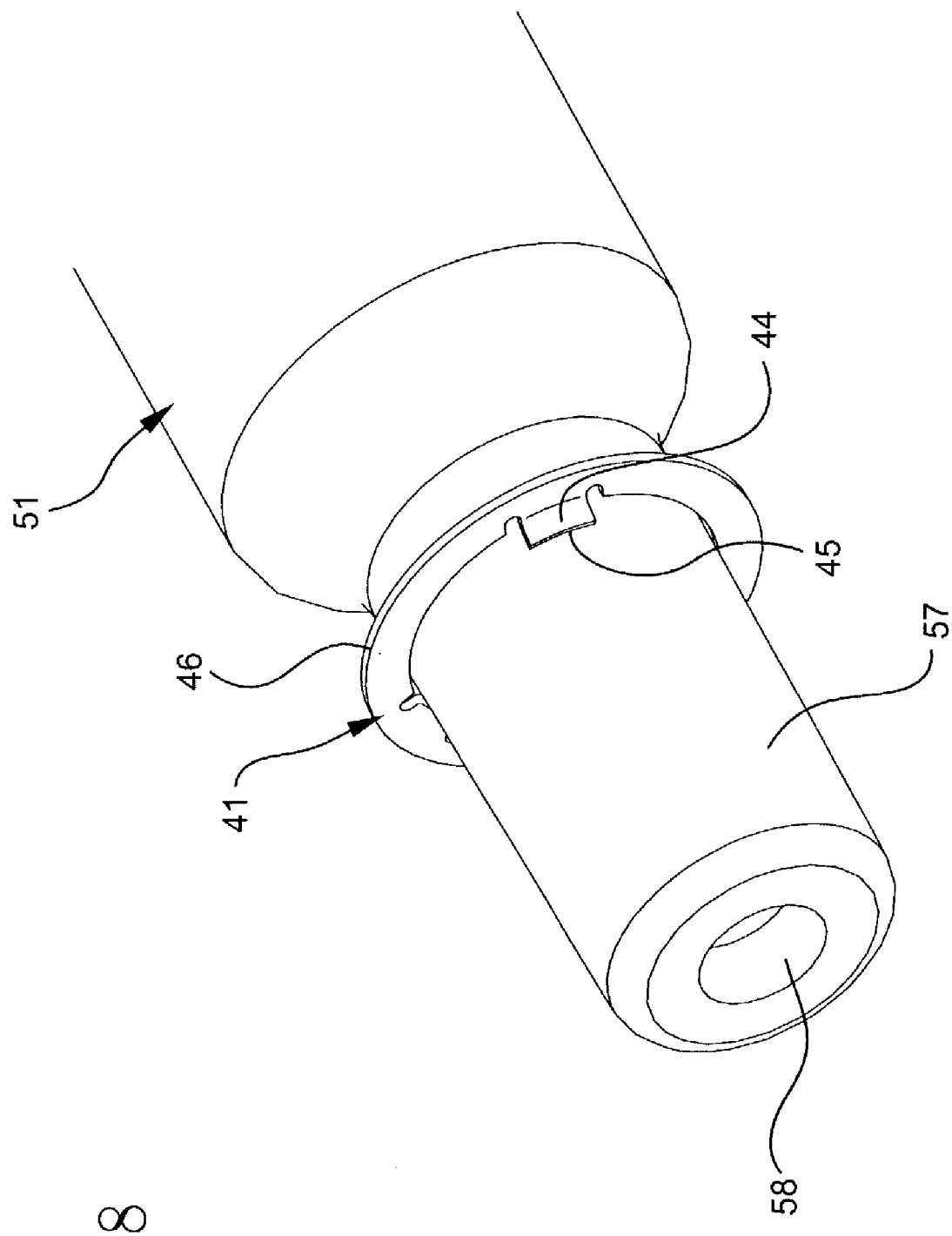
FIG. 8 is a perspective view of the distal end of the syringe barrel with retaining element attached thereto.

In use, as best illustrated in FIGS. 5–8, needle assembly 20 is connected to syringe barrel 51 by placing the elongate frusto-conically shaped barrel tip into the frusto-conically shaped cavity of the needle hub and applying an axial force sufficient to frictionally engage the surface of the hub cavity and the outside surface of the barrel tip as illustrated in FIG. 7. During installation, the retaining element slides down the barrel tip eventually contacting the barrel tip with enough force to engage the tip and make it more difficult to move the element in a distal direction than in a proximal direction. The element can provide additional retaining force. To remove the needle assembly, an axially distally directed force is applied to the needle hub until the retaining element disconnects from the hub and the needle assembly is allowed to move in a distal direction. As illustrated in FIG. 8, the retaining element remains on the barrel tip after removal of the needle hub and needle combination. Additional needle assemblies such as the needle assembly of the present invention or a standard needle assembly can be subsequently connected to the syringe tip having the retaining element attached thereto because the installation force will move the retaining element in a proximal direction to make room for the subsequent needle assembly to frictionally engage the barrel tip.

Figure 9:
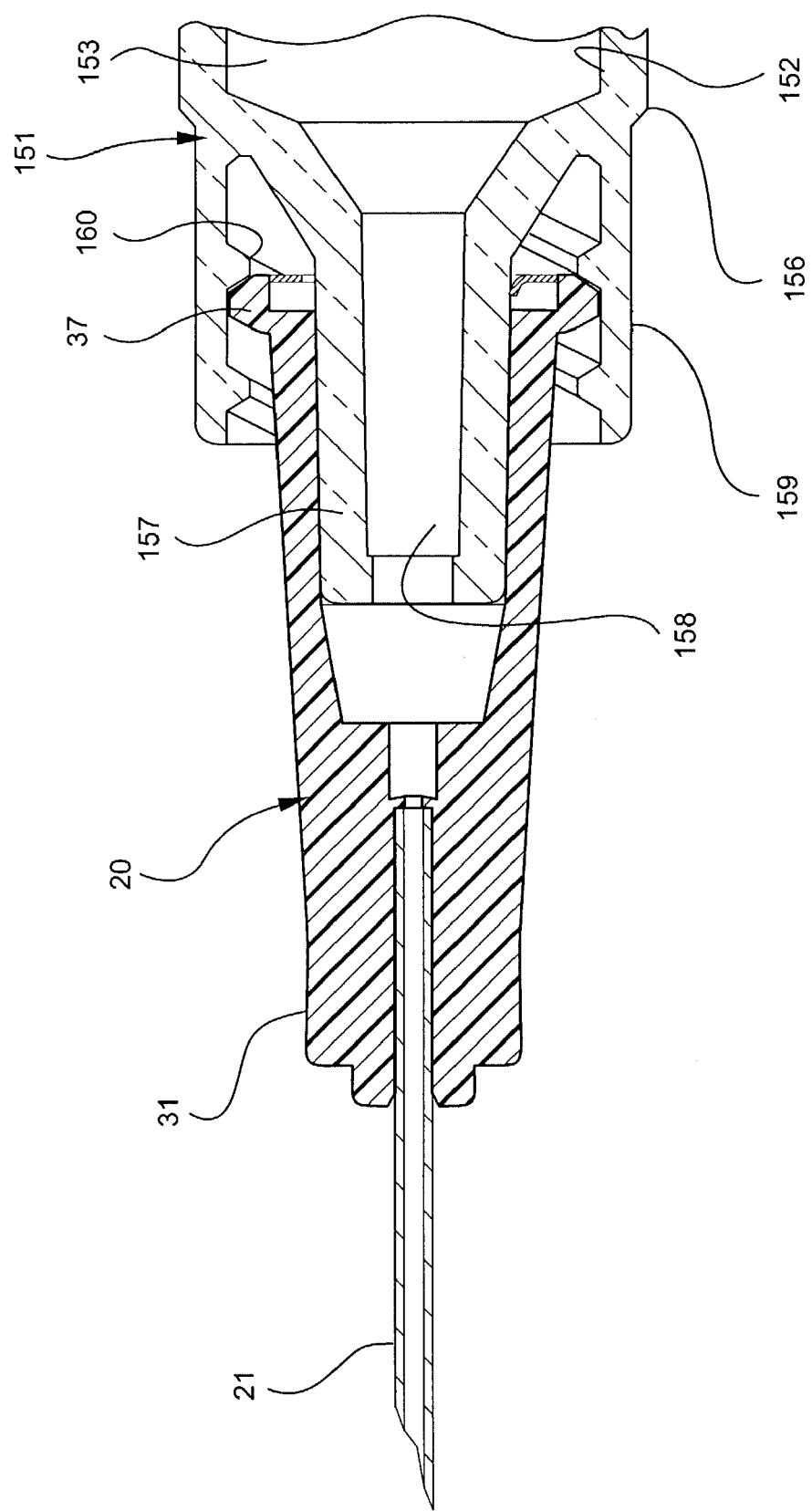
FIG. 9 is a partial cross-sectional view illustrating the needle assembly of the present invention attached to a syringe barrel having a locking luer collar.

Another advantage of the needle assembly of the present invention is that it can be used with syringe barrels having a locking luer collar. Although the primary advantage of the present invention is achieved with its use with a luer slip syringe barrel it will also function with a syringe barrel having a locking luer collar. This is an advantage for the user with respect to inventory, since separate needle assemblies will not have to be purchased for use with different types of syringe barrels. As best illustrated in FIG. 9, a syringe barrel 151 includes an inside surface 152 defining a chamber 153, and a distal end 156 including an elongate frusto-conically shaped tip 157 having a conduit 158 therethrough. The distal end of the syringe barrel also includes a locking luer-type collar 159 concentrically surrounding tip 157 of the barrel. The luer collar has an internal thread 160 which engages radial projections 37 on the hub to hold it securely to the barrel.

Figure 10:
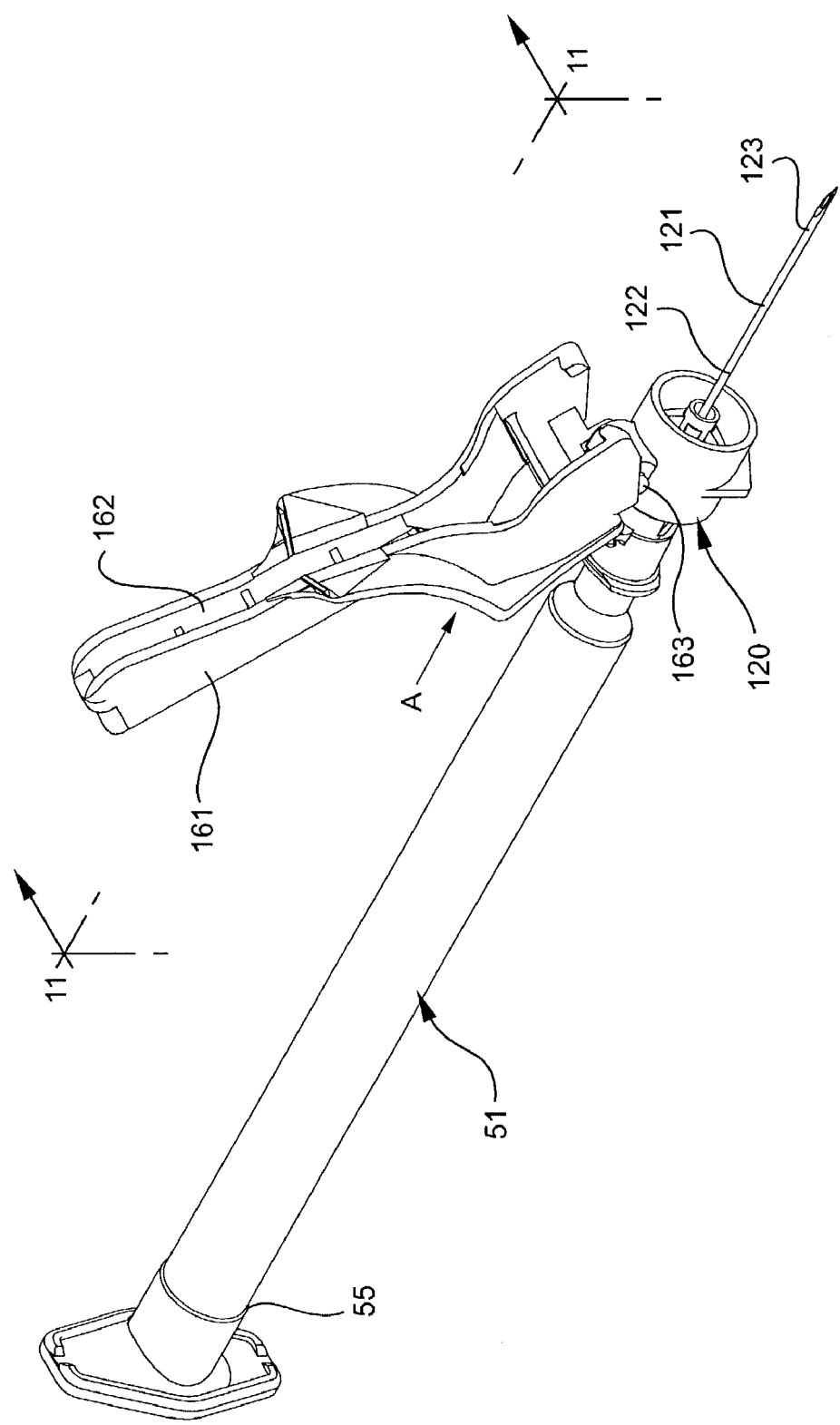
FIG. 10 illustrates an alternative embodiment of the needle assembly of the present invention having a pivotable needle shield.
Figure 11:
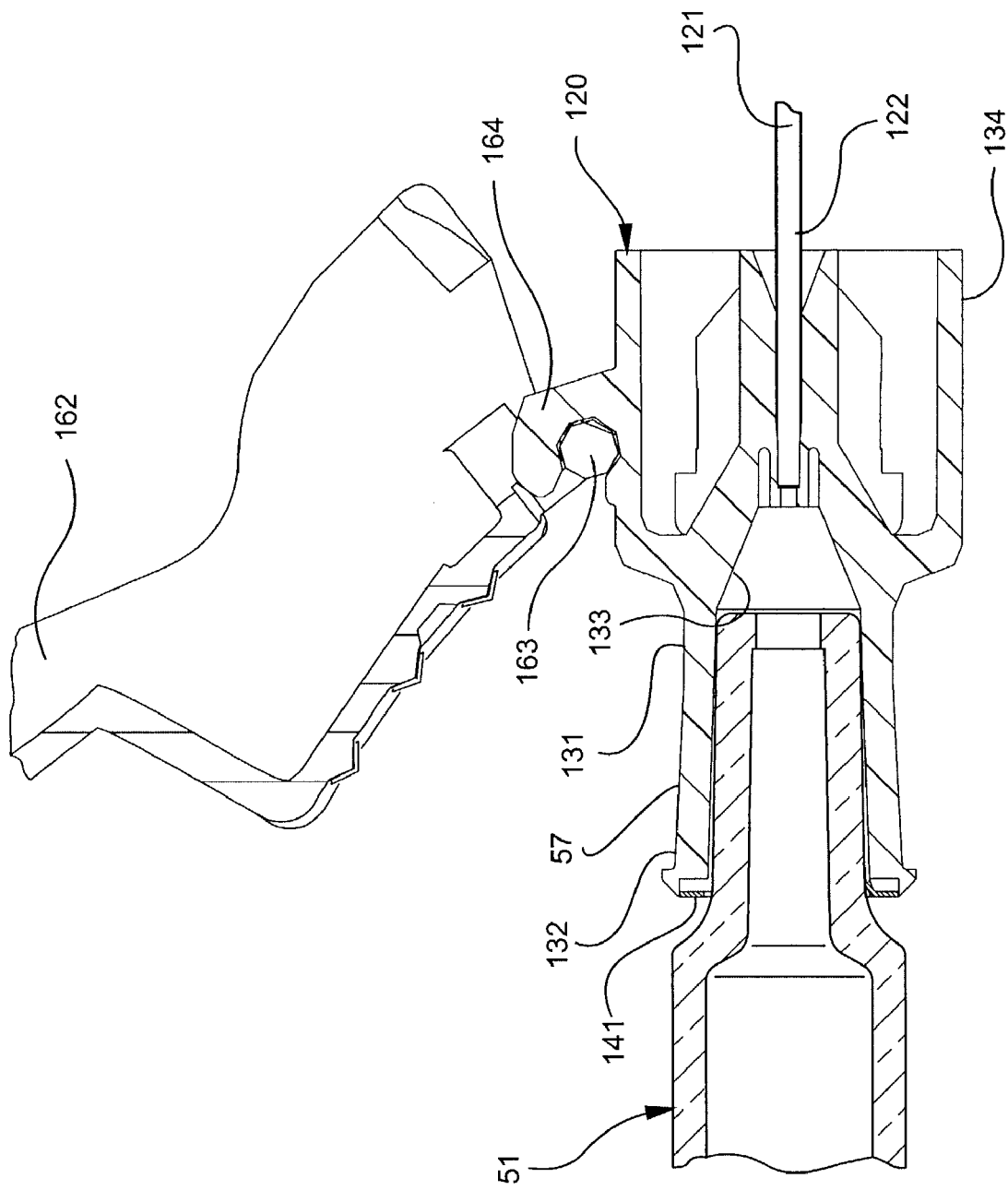
FIG. 11 is an enlarged cross-sectional view of the syringe barrel and needle assembly of FIG. 10 taken along line 11—11.

FIGS. 10–11 illustrate an alternative embodiment of the needle assembly of the present invention. In this embodiment, needle assembly 120 includes a needle cannula 121 having a proximal end 122 and a distal end 123 and a hub 131. Hub 131 includes an open proximal end 132 with a frusto-conically shaped cavity 133, a distal end 134, a passageway 135 therethrough. The cavity is part of the passageway. The proximal end of the needle cannula is joined to the distal end of the hub so that the lumen of the needle cannula is in fluid communication with the passageway. A retaining element 141 is releasably connected to hub 131. The retaining element includes an aperture therein and at least one protuberance projecting into the aperture for engaging the frusto-conically shaped tip 57 of the barrel. As with the embodiment of FIGS. 1–8, the protuberance is shaped to offer less resistance to hub movement in a direction of engagement than in a direction of disengagement with the barrel tip. The retaining element is connected to the hub so that when the hub is in fluid-tight engagement with the tip, the force required to disengage the retaining element from the tip is greater than the force required to disengage the retaining element from the hub. Hub 131 further includes pivotable needle shield 161 which is hingedly connected to the hub and capable of pivoting from a needle exposing position, as illustrated in FIGS. 10–11, which allows access to the distal end of the needle cannula and a needle protecting position wherein the distal end of the needle cannula is within cavity 162 of the needle shield. The structure used to provide the pivotable relationship between the hub and the needle shield can include a variety of hinges linkages, living hinges and the like. In this embodiment axel 163 rotatably engages axel housing 164 on the hub.

After use, the user pivots the needle shield into the needle protecting position by applying digital force to the needle shield. Such force has at least a component in direction A as illustrated in FIG. 10. The present invention is especially useful as a hinged needle shield needle assembly. Force A is another force which may contribute to the unintentional disconnection of the needle assembly from the barrel which is resisted by action of the retaining elements' engagement to the barrel tip.

Figure 12:
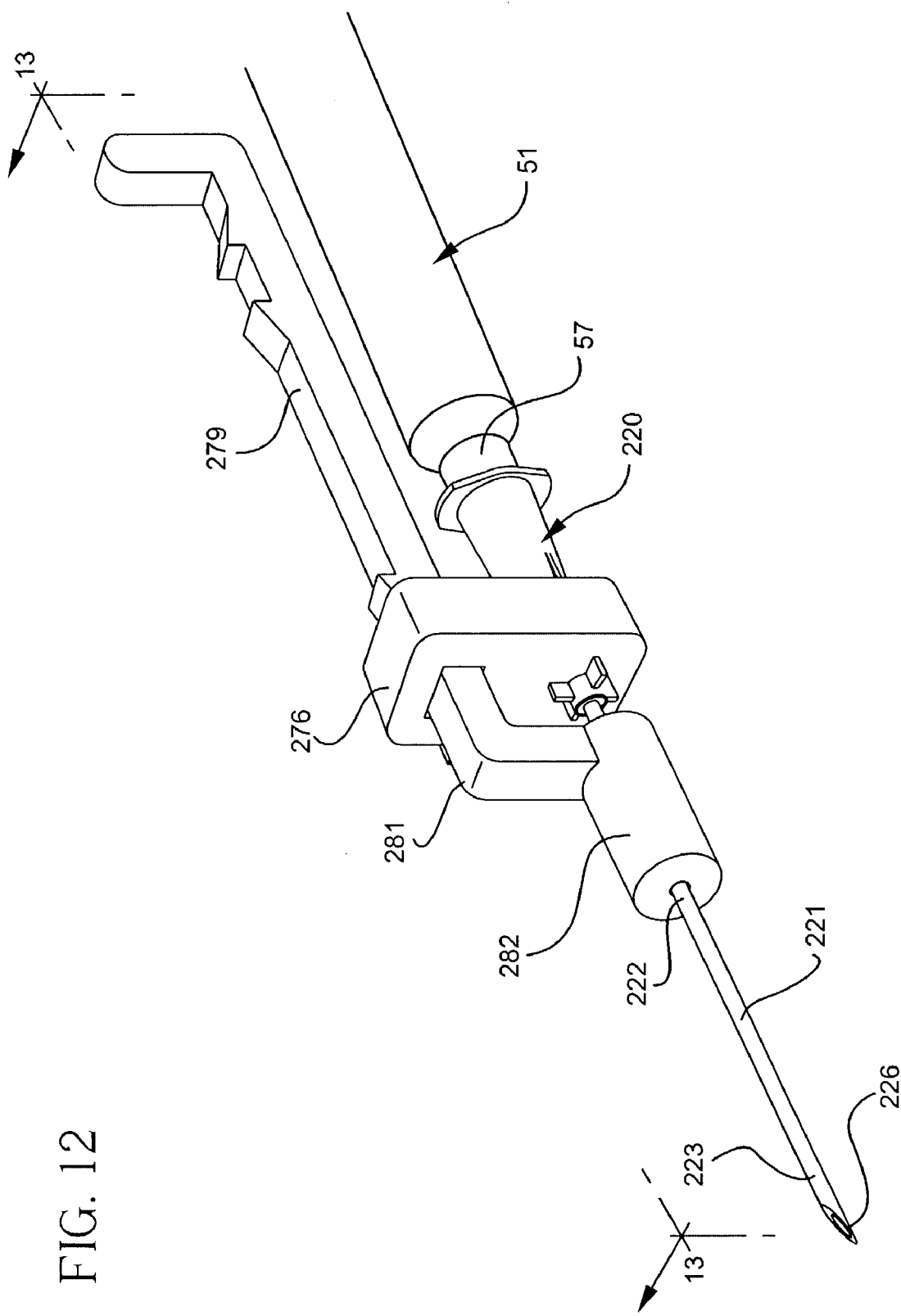
FIG. 12 is a perspective view of an alternative embodiment of the needle assembly of the present invention illustrated after frictional engagement with a syringe barrel tip.
Figure 13:
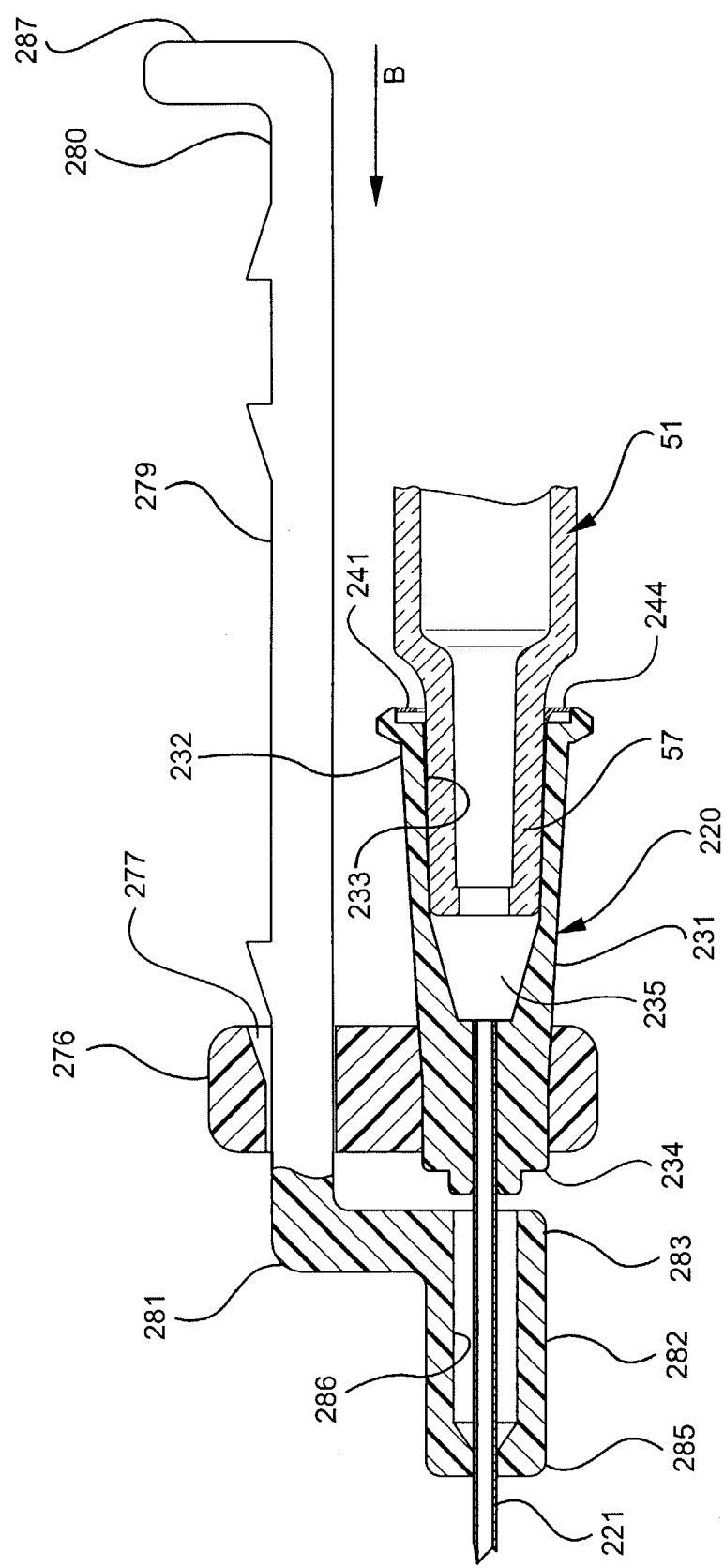
FIG. 13 is a cross-sectional view of the needle assembly and syringe barrel of FIG. 12 taken along line 13—13.

FIGS. 12 and 13 illustrate another alternative embodiment of the medical device of the present invention. In this embodiment, needle assembly 220 includes a needle cannula 221 having a proximal end 222, a distal end 223 and a lumen therethrough. A hub 231 includes an open proximal end 232 with a frusto-conically shaped cavity 233 therein, a distal end 234 and a passageway 235 therethrough. The cavity is part of the passageway. The proximal end of the needle cannula is joined to the distal end of the hub so that the lumen is in fluid communication with the passageway. A retaining element 241 is releasably connected to the hub. The retaining element has at least one protuberance 244 for engaging frusto-conically shaped tip 57 of syringe barrel 51. The protuberance is shaped to offer less resistance to hub movement in a direction of engagement with the syringe barrel tip than in a direction of disengagement with the tip. The retaining element of this embodiment functions substantially similarly to retaining element 41 of the embodiments of FIGS. 1–8. Hub 231 further includes a guide element 276 having an aperture 277 therethrough. An elongate barrier arm 279 having a proximal end 280 and a distal end 281 includes a barrier element 282 on distal end 281. The barrier element includes a proximal end 283, a distal end 285 and a needle passageway 286 therethrough. The barrier arm is positioned within the aperture of the guide element and the needle cannula is positioned at least partially within the needle passageway of the barrier element. The barrier element is movable from at least a first retracted position, illustrated in FIGS. 12–13, wherein the distal end of the needle cannula passes completely through the barrier element so that the distal end of the needle cannula is exposed, to a second extended position (not illustrated) wherein the barrier element surrounds the distal end of the needle cannula to prevent incidental contact with tip 226 on the distal end of the needle cannula. A finger contact surface 287 on the barrier arm is provided for applying digital force to the barrier arm to move the barrier arm into the second extended position. This is accomplished by applying a digital force to the finger contact surface having at least a component in direction B as illustrated in FIG. 13. The aperture in the guide element can be any shape, closed or open, which works cooperatively to guide the barrier arm between the first retracted position and the second extended position. The barrier arm may be curved or the aperture in the guide element angled so that the needle passageway misaligns with tip 326 on the needle cannula to help prevent movement of the barrier element from the second extended position.

Figure 14:
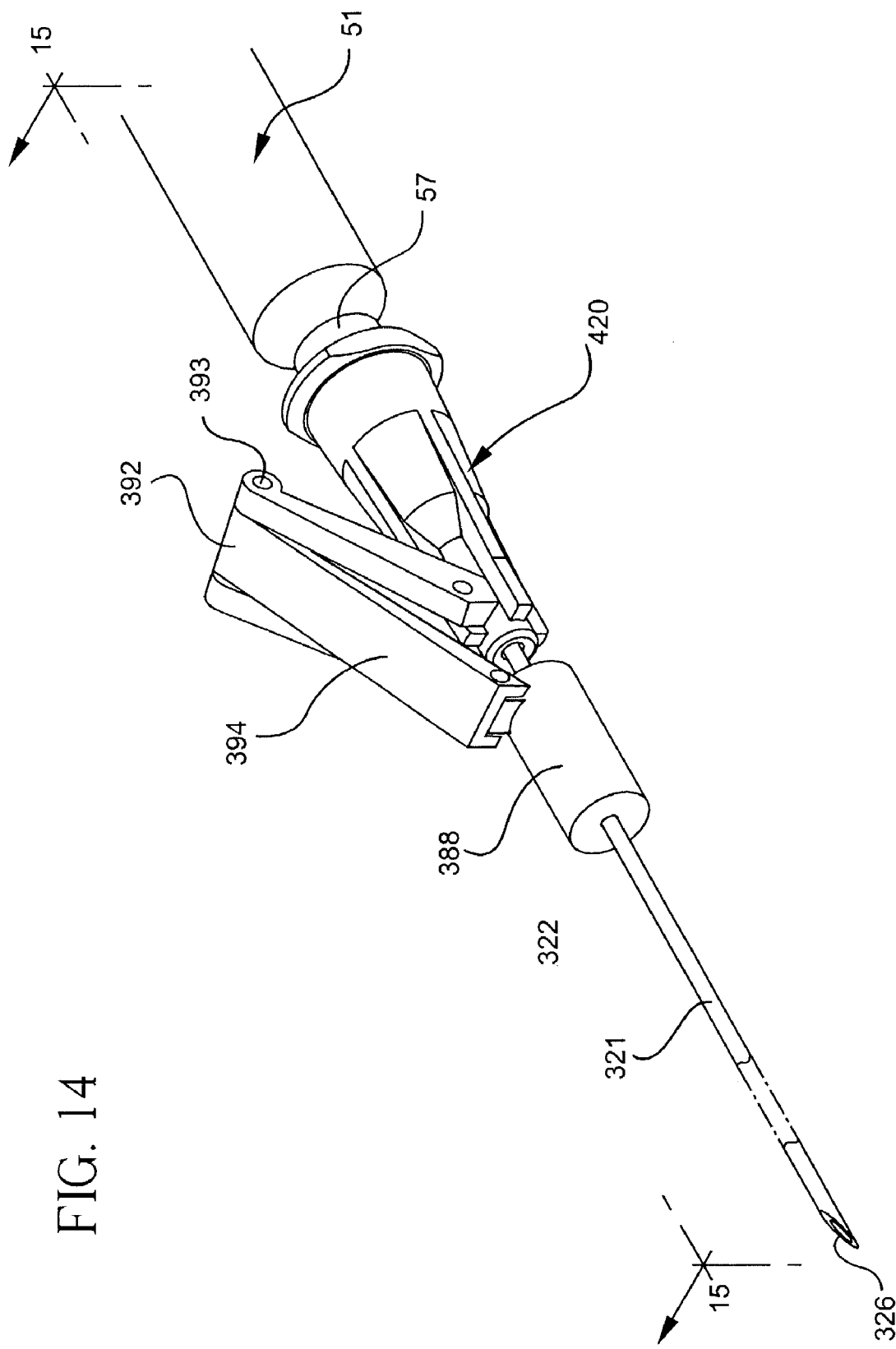
FIG. 14 is a perspective view of another alterative embodiment of the needle assembly of the present invention illustrated after frictional engagement with a syringe barrel tip.
Figure 15:
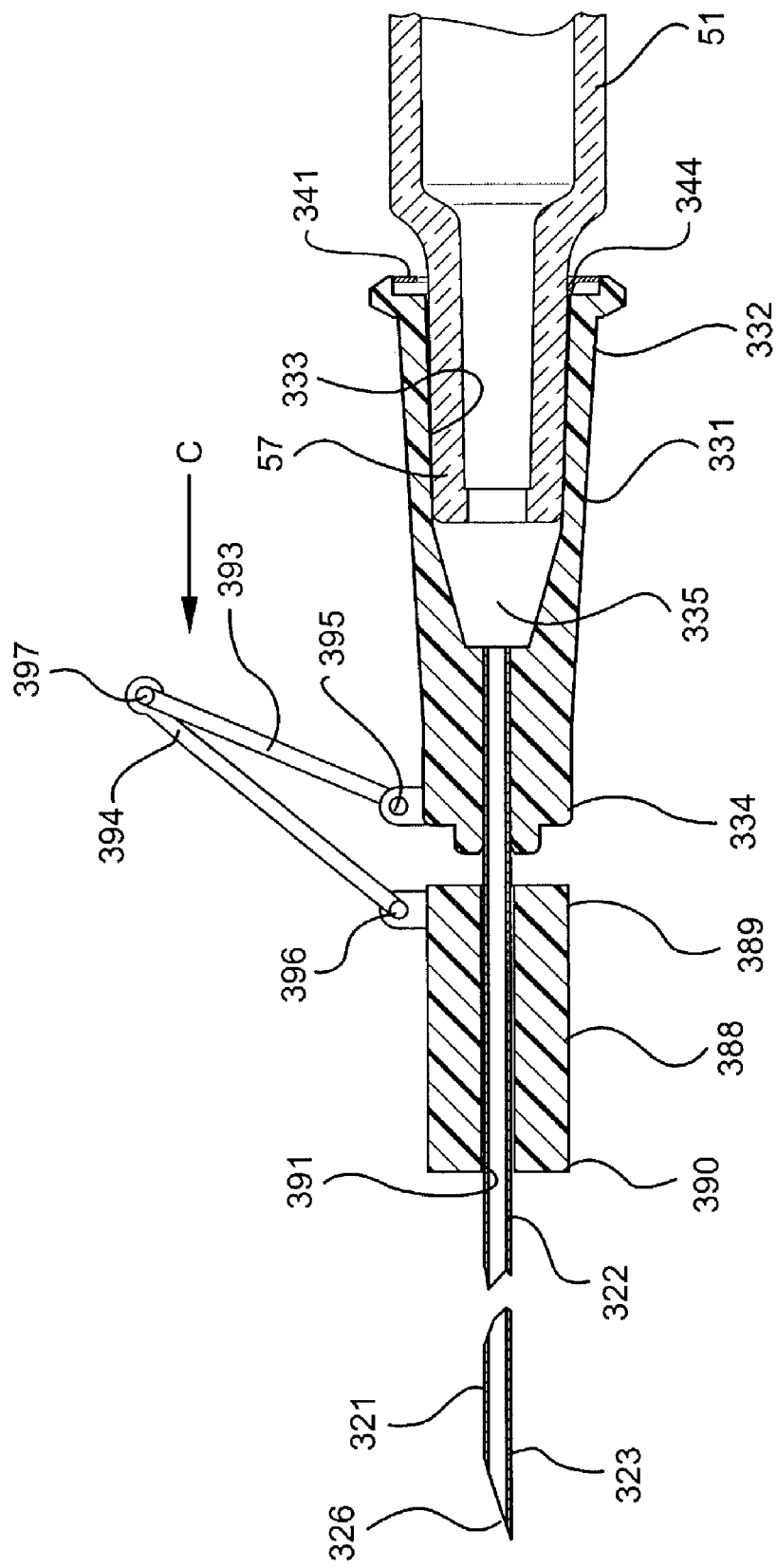
FIG. 15 is a cross-sectional view of the needle assembly and syringe barrel of FIG. 14 taken along line 15—15.

FIGS. 14–15 illustrate another alternative embodiment of the needle assembly of the present invention. In this embodiment, needle assembly 320 includes a needle cannula 321 having a proximal end 322, a distal end 323 and a hub 331. Hub 331 includes an open proximal end 332 with a frusto-conically shaped cavity 333, a distal end 334 and a passageway 335 therethrough. The cavity is part of the passageway. The proximal end of the needle cannula is joined to the distal end of the hub so that the lumen of the needle cannula is in fluid communication with the passageway. A retaining element 341 is releasably connected to the hub. Retaining element includes at least one protuberance 344 for engaging frusto-conically shaped tip 57 of syringe barrel 51. Retaining element 341 functions similarly to retaining element 41 in the embodiment of FIGS. 1–8. Needle assembly 320 further includes a needle guard 388 having a proximal end 389, a distal end 390 and a needle passageway 391 therethrough. The needle guard is movable along the needle cannula from a first position substantially adjacent to the proximal end of the needle cannula as illustrated in FIGS. 14–15, to a second position where the distal tip 326 of the needle cannula is intermediate the opposed proximal and distal ends of needle guard 388. A hinged arm 392 having a proximal segment 393 and a distal segment 394 which are articulated to one another for movement between a first position where the segments are substantially collapsed onto one another, as illustrated in FIGS. 14–15, to a second position where the segments are extended from one another. The proximal segment of the hinged arm is articulated to a portion of the hub through a structure that allows such movement, such as hinged 395 in this embodiment. The distal segment of the hinged arm is articulated to needle guard 388 through hinge 396. Proximal segment 393 and distal segment 394 are articulated with respect to each other through hinge 397. The proximal and distal segments of the hinged arm have respective lengths for permitting the needle guard to move from the first position to the second position on the needle cannula and for preventing the guard from moving distally beyond the second position. The needle guard is moved to the second position through application of a digital force having at least a component in direction C as illustrated in FIG. 15. The hinges may be mechanical hinges or linkages or flexible connections such as living hinges.

Figure 16:
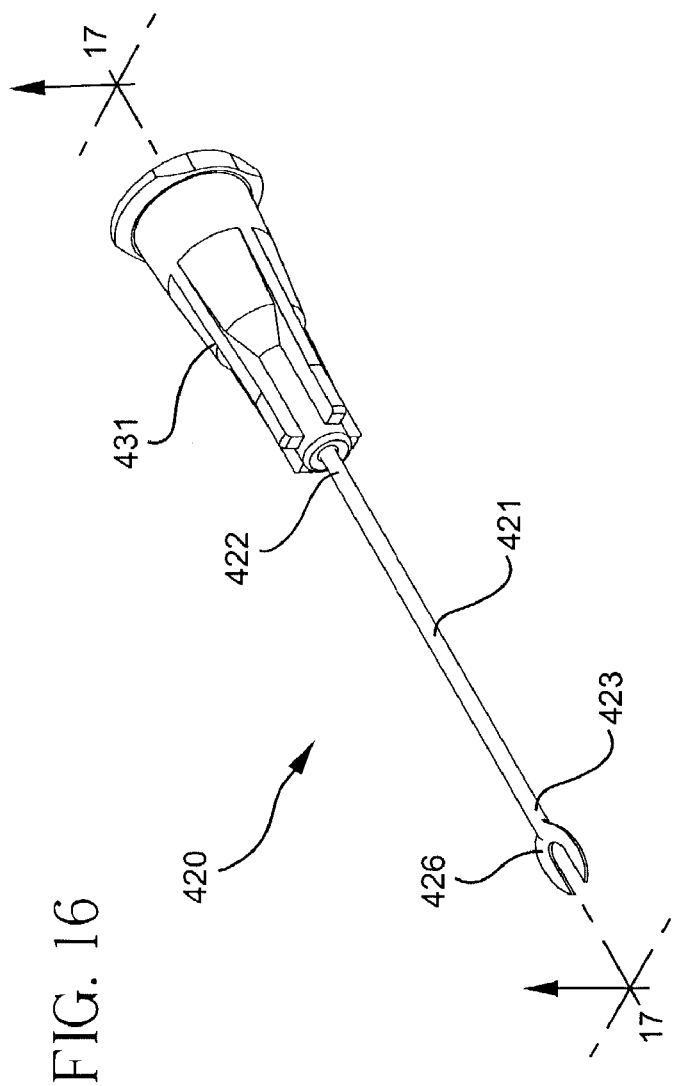
FIG. 16 is a perspective view of another alternative needle assembly of the present invention.
Figure 17:
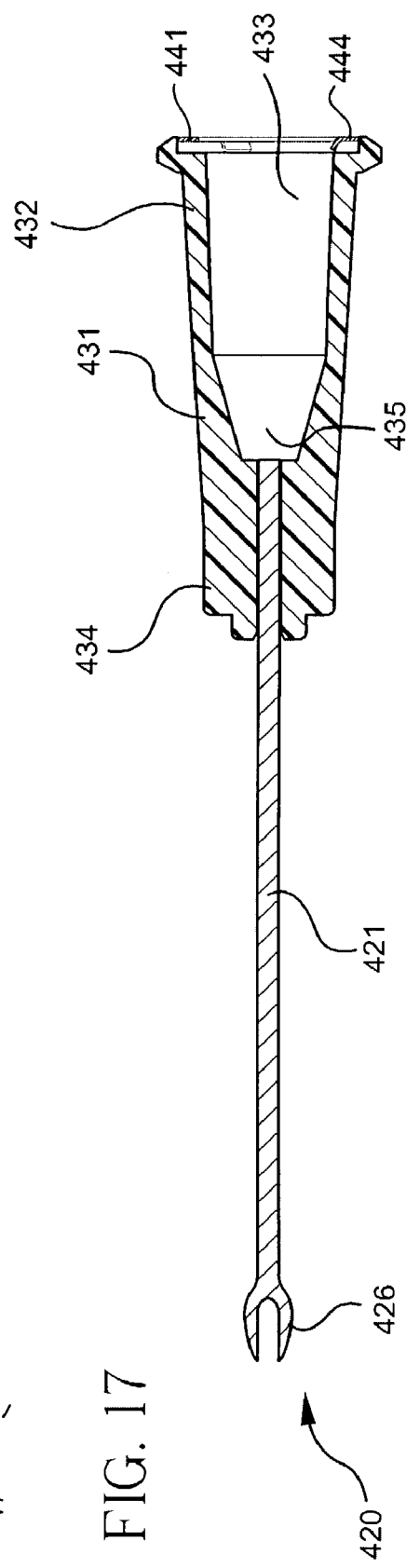
FIG. 17 is an enlarged cross-sectional view of the needle assembly of FIG. 16 taken along line 17—17.

FIGS. 16–17 illustrate another embodiment of the needle assembly of the present invention. In this embodiment, needle assembly 420 includes a needle 421 having a proximal end 422, a distal end 423 and a hub 431. Hub 431 includes an open proximal end 432 with a frusto-conically shaped cavity 433, a distal end 434 and a passageway 435 therethrough. The cavity is part of the passageway. The proximal end of the needle is joined to the distal end of the hub so that the needle projects distally outwardly from the distal end of the hub. A retaining element 441 is releasably connected to the hub. Retaining element 441 includes at least one protuberance 444 for engaging a frusto-conically shaped tip of a fluid delivery device such as a syringe barrel. Release element 441 functions similarly to release element 41 in the embodiment of FIGS. 1–8. Needle 421 does not have a functioning lumen and in this embodiment, has a bifurcated distal tip 426. Solid needles such as the needle having a bifurcated tip are commonly used for administering vaccines, antigens, and other substances to the skin. The bifurcated tip is used to scratch or slightly pierce the skin of the patient so that the liquid substance, such as a vaccine, may be absorbed into the skin of the patient. The needle assembly of this embodiment can be attached to a syringe barrel, wherein the syringe barrel is used as a handle to control and guide the needle tip during the vaccination process.

What is claimed is:

1. A medical device for use with a fluid transfer device having a frusto-conically shaped tip comprising:
   a hub having an open proximal end with a frusto-conically-shaped cavity therein, a distal end and a passageway therethrough, said cavity being part of said passageway;
   a retaining element releasably connected to said hub at a proximal end of said cavity, said element having an aperture therein and a plurality of protuberances projecting into said aperture for engaging said frusto-conically shaped tip, at least one of said protuberances being shaped to offer less resistance to hub movement in a direction of engagement than in a direction of disengagement with said tip, means for connecting said retaining element to said hub so that when said hub is in fluid-fight engagement with said tip, the force required to disengage said retaining element from said tip is greater than the force required to disengage said retaining element from said hub; and
   a cannula having a proximal end, a distal end a lumen therethrough, said proximal end of said cannula being joined to said distal end of said hub so that said lumen is in fluid communication with said passageway.

2. The medical device of claim 1 wherein said cannula is an elongate needle.

3. The medical device of claim 1 wherein said plurality of protuberances is three protuberances spaced around said aperture.

4. The medical device of claim 1 wherein said means for connecting is an interference fit between said retaining element and said hub.

5. The medical device of claim 1 wherein said retaining element completely surrounds said passageway.

6. The medical device of claim 1 wherein said retaining element is made of metal.

7. The medical device of claim 6 wherein said metal is stainless steel.

8. The medical device of claim 1 wherein said hub is made of thermoplastic material.

9. The medical device of claim 1 further including a syringe barrel having an inside surface defining a chamber, an open proximal end and a distal end including an elongate frusto-conically shaped tip having a conduit therethrough, said hub being connected to said syringe barrel so that said frusto-conically shaped tip is in fluid-tight engagement with said frusto-conically shaped cavity of said hub and said lumen is in fluid communication with said cavity.

10. A needle assembly for use with a fluid transfer device having a frusto-conically shaped tip comprising:
   a needle cannula having a proximal end, a sharp distal end and a lumen therethrough;
   a hub having an open proximal end with a frusto-conically shaped cavity therein, a distal end and a passageway therethrough, said cavity being part of said passageway, said proximal end of said needle cannula being connected to said distal end of said hub so that said lumen is in fluid communication with said passageway; and
   a metal retaining element releasably connected to said hub at a proximal end of said cavity, said element having an aperture therein and a plurality of protuberances projecting into said aperture for engaging said frusto-conically shaped tip, said protuberances being shaped to offer less resistance to hub movement in a direction of engagement than in a direction of disengagement with said tip, said retaining element and said hub being configured to be held together by an interference fit so that when said hub is in fluid-tight engagement with said tip, the force required to disengage said retaining element from said tip is greater than the force required to disengage the retaining element from said hub.

11. The needle assembly of claim 10 further including a syringe barrel having an inside surface defining a chamber, an open proximal end and a distal end including an elongate frusto-conically shaped tip having a conduit therethrough, said needle assembly being connected to said syringe barrel so that said frusto-conically shaped tip is in fluid-tight engagement with said frusto-conically shaped cavity of said hub and said lumen is in fluid communication with said cavity.

12. A needle assembly for use with a fluid transfer device having a frusto-conically shaped tip comprising:
   a needle cannula having a proximal end, a distal end and a lumen therethrough;
   a hub having an open proximal end wit a frusto-conically-shaped cavity therein, a distal end and a passageway therethrough, said cavity being part of said passageway, said proximal end of said needle cannula being joined to said distal end of said hub so that said lumen is in fluid communication with said passageway; and
   a retaining element releasably connected to said hub at a proximal end of said cavity, said element having an aperture therein and at least one protuberance projecting into said aperture for engaging said frusto-conically shaped tip, said protuberance being shaped to offer less resistance to hub movement in a direction of engagement than in a direction of disengagement with said tip, means for connecting said retaining element to said hub so that when said hub is in fluid-tight engagement with said tip, the force required to disengage said retaining element from said tip is greater than the force required to disengage said retaining element from said hub.

13. The needle assembly of claim 12 further including a syringe barrel having an inside surface defining a chamber, an open proximal end and a distal end including an elongate frusto-conically shaped tip having a conduit therethrough, said medical device being connected to said syringe barrel so that said frusto-conically shaped tip is in fluid-tight engagement with said frusto-conically shaped cavity of said hub and said passageway is in fluid communication with said cavity.

14. A medical device for use with a fluid transfer device having a frusto-conically shaped tip comprising:
   a hub having an open proximal end with a frusto-conically-shaped cavity therein, a distal end and a passageway therethrough, said cavity being part of said passageway;
   a retaining element releasably connected to said hub at a proximal end of said cavity, said element having an aperture therein and at least one protuberance projecting into said aperture for engaging said frusto-conically shard tip, said protuberance being shaped to offer less resistance to hub movement in a direction of engagement than in a direction of disengagement with said tip, means for connecting said retaining element to said hub so that when said hub is in fluid-tight engagement with said tip, the force required to disengage said retaining element from said tip is greater than the force required to disengage said retaining element from said hub; and a cannula having a proximal end, a distal end and a lumen therethrough, said proximal end of said cannula being joined to said distal end of said hub so that said lumen is in fluid communication with said passageway; and a syringe barrel having an inside surface defining a chamber, an open proximal end and a distal end including an elongate frusto-conically shaped tip having a conduit therethrough, said hub being connected to said syringe barrel so that said frusto-conically shaped tip is in fluid-tight engagement with said frusto-conically shaped cavity of said hub and said lumen is in fluid communication with said cavity.

15. The medical device of claim 14 wherein said retaining element completely surrounds said passageway.

* * * * *